United States Patent [19]

Chirife

[11] Patent Number: 5,168,869
[45] Date of Patent: Dec. 8, 1992

[54] RATE RESPONSIVE PACEMAKER CONTROLLED BY ISOVOLUMIC CONTRACTION TIME

[76] Inventor: Raul Chirife, Pirovano 137, 1640 Martinez, Buenos Aires, Argentina

[21] Appl. No.: 716,405

[22] Filed: Jun. 17, 1991

[51] Int. Cl.⁵ .............................. A61N 1/36
[52] U.S. Cl. .............................. 128/419 PG
[58] Field of Search ................. 128/419 PL

[56] References Cited

U.S. PATENT DOCUMENTS

| | | | |
|---|---|---|---|
| 4,485,813 | 12/1984 | Anderson et al. | 128/419 P X |
| 4,686,987 | 10/1987 | Salo et al. | 128/419 PG |
| 4,708,143 | 11/1987 | Schroeppel | 128/419 PG |
| 4,719,921 | 1/1988 | Chirife | 128/419 PG |
| 4,730,619 | 3/1988 | Koning et al. | 128/419 PG |
| 4,733,667 | 3/1988 | Olive et al. | 128/419 PG |
| 4,773,401 | 9/1988 | Citak et al. | 128/419 PG |
| 4,856,524 | 8/1989 | Baker, Jr. | 128/419 PG |
| 4,865,036 | 9/1989 | Chirife | 128/419 D |
| 4,873,980 | 10/1989 | Schaldach | 128/419 PG |
| 4,884,576 | 12/1989 | Alt | 128/419 PG |
| 4,890,617 | 1/1990 | Markowitz | 128/419 PG |
| 4,919,137 | 4/1990 | Schaldach | 128/419 PG |
| 4,936,304 | 6/1990 | Kresh | 128/419 PG |
| 5,024,222 | 6/1991 | Thacker | 128/419 PG |

Primary Examiner—Lee S. Cohen
Assistant Examiner—Jeffrey R. Jastrzab
Attorney, Agent, or Firm—Haugen and Nikolai

[57] ABSTRACT

A rate responsive pacemaker uses isovolumic contraction time (IVCT) as a control signal responsive to metabolic demands. This control signal is injected into the timing circuit of a standard rate adaptive pacemaker to enhance the pacer's ability to respond in direct relation to the patient's changing metabolic needs as he performs his daily activities. A typical configuration, uses the duration of either right or left heart IVCT for rate control. The device has two inputs to measure IVCT: one, signaling the onset of mechanical activation of the ventricle, and another, signaling the onset of ejection. The time interval between these two signals is the duration of IVCT, which is processed by the pacemaker to determine the escape interval.

13 Claims, 2 Drawing Sheets

RATE RESPONSIVE PACEMAKER CONTROLLED BY ISOVOLUMIC CONTRACTION TIME

BACKGROUND OF THE INVENTION

I. Field of the Invention

This invention relates generally to the design of cardiac pacemakers and more particularly to the timing control of a rate responsive cardiac pacer. The isovolumic contraction time (IVCT) of a beating heart is used as a control parameter for a rate adaptive cardiac pacer. Thus, the pacer is responsive to metabolic demand.

II. Discussion of the Prior Art

Patients who suffer from severe bradycardia or chronotropic incompetence require implantation of a cardiac pacemaker in order to restore a normal resting heart rate. Such pacers usually have a fixed rate or a narrow range of externally programmable rates, so they are also efficacious in meeting metabolic demand at low levels of exercise. However, the inadequacy of a fixed pacing rate or a narrow range to meet metabolic demands at rest and during exercise led to the development of rate responsive pacemakers. Rate responsive pacers were developed to provide a rate increase that is commensurate with prevailing metabolic demand. The pacer assesses metabolic demand by a variety of methods, then automatically adjusts its escape interval upwards or downwards to provide a cardiac output commensurate with this demand. Such pacers are an improvement over the fixed rate pacers, but some models available on the market suffer from either a lack of sensitivity to changing conditions indicative of metabolic demand, a lack of specificity or a lack of sufficient speed in response to changes. An example of pacers that suffer from a lack of specificity are those that are controlled by activity detectors. For example, the Activitrax ® pacer sold by Medtronic, Inc. uses body motion or various vibrations as a basis for developing a rate adjusting control signal. Difficulty arises in distinguishing these motions or vibrations from artifacts produced by passive vibration or by motion that is not associated with a metabolic demand increase. The control signal is introduced into the timing sensor of the pacer, resulting in an inappropriate rate response.

Other relatively nonspecific pacers are those that base motion detection on respiration parameters, such as transthoracic impedance. The respiratory impedance signal obtained in this manner is commonly contaminated by body motion artifacts, such as arm movements, which unduly increase the rate beyond what is dictated by the prevailing metabolic needs.

A lack of sensitivity is common in temperature-controlled pacers. There exists a normal physiologic lag between onset and level of exercise and the point at which the body temperature rises by an amount that will alter the pacer's rate. This slow response can also be unpredictable. Pacers using QT interval as a control parameter are also relatively slow in reacting to changed metabolic needs. They tend to be non-specific and some are erratic. Self-acceleration is common in these pacers, because the physiologic signal used for rate control predisposes them to positive feedback.

As is explained in my earlier U.S. Pat. No. 4,719,921, these difficulties are overcome by use of a pacer algorithm for a rate adaptive pacer based upon pre-ejection period (PEP). This biological signal seems to be ideal for controlling pacing in such rate adaptive pacemakers, since it is fast, specific and sensitive. PEP is the time interval either from the onset of QRS or from the pacing spike, whichever occurs first, to the onset of ventricular ejection. Furthermore, PEP is linearly related to ECG cycle length variation induced by changing metabolic needs. To practically implement a PEP-controlled pacemaker, the signal from which PEP is measured should be obtained directly from within the heart. It is recommended that this signal be derived via the impedance technique, since it permits the detection of a right ventricular volume waveform from which PEP can be measured using conventional pacing leads. For example, the onset of ventricular ejection can be derived from the right ventricular impedance signal, which is inversely proportional to ventricular volume. Thus, a sudden rise in impedance indicates a sudden reduction in ventricular volume, which in turn is indicative of the onset of ejection. Using this type of measuring device, PEP is consequently re-defined as the interval from the QRS or pacing spike to a sudden increase in ventricular impedance. PEP is thus an electromechanical interval, comprised of two major sub-components: the electro-mechanical lag (EML), which is the time from the onset of electrical activity, to the onset of mechanical activation of the ventricle, and the isovolumetric contraction time (IVCT), which goes from the onset of mechanical activation to the onset of ventricular ejection.

The artificial electronic pacemaker described in the aforereferenced patent is adapted to alter the stimulus pulse rate of its pacing pulse generator in response to metabolically determined variations in PEP which parallel the normal atrial rate variations from the same stimuli. In this manner, rate is adjusted as a function of the cardiac output requirements of the body so that rate is commensurate with the needs of the individual. An electric signal that depends on the PEP is used to regulate the pulse generator's escape interval in any of the conventional pacing modes, including the AAI, VVI, DVI, VDD and DDD modes. Specifically, this pacemaker system comprises a first device that senses the beginning of each natural QRS waveform in the ECG signal. If there is no natural QRS signal within an escape interval to cause the heart to beat, then the artificial stimulus pulse provided as a substitute by the pacemaker is sensed. In either case, the sensed signal corresponds to the time the heart is being signaled to initiate ventricular contraction. After a delay extending to the beginning of the IVCT, the ventricles begin to contract, but blood is not yet being ejected. A second sensor is used to detect the precise moment the blood pressure in the contracting ventricle equals the static diastolic pressure in the aorta or pulmonary artery or when blood begins to flow in these vessels or other arteries. This time corresponds to the onset of ventricular ejection and constitutes the end of the PEP. Thus, using the time of the beginning of the QRS complex and the time of the subsequent signal indicative of ventricular ejection being sensed, the time interval between the two represents the PEP. A signal proportional to the variable PEP and, hence, to variable physiological requirements is used to adjust the pacemaker's escape interval and, therefore, its stimulation pulse rate.

The use of PEP as a control parameter is not without some complications because several physiological conditions exist that are not adequately sensitive to PEP as a control parameter. Among these are right bundle branch block (RBBB) and left ventricular extrasystoles.

Bundle branch block is a conduction abnormality within specialized fibers of the ventricular walls. The Purkinje system, including the bundle branches, is a branching complex of nervous tissue, specialized for the conduction of electrical depolarizations through the central regions of the heart. These specialized tissues permit a much more rapid conduction of the heart beat to occur than would ordinarily exist if the electrical depolarization were simply transferred from cardiac cell to cardiac cell. This blockage of conduction need not be complete. The depolarization can follow an altered pathway and thus be manifested as a lengthened depolarization interval on a standard electrocardiogram of the ventricle (e.g., QRS complex). These bundle branch blocks are usually assumed to be related to a specific lesion in one of the major divisions of this nervous system, whether left or right. However, some are not explained on this basis alone and are thought to be related to disease states of the ventricles, such as myocardial hypertrophy (heart enlargement). Right bundle branch block involves the portion of this conduction system that supplies the contraction stimulus to the right ventricle. This condition causes the overall ventricular depolarization (QRS) to be lengthened, due to a synchronous excitation of the two ventricles. In the presence of right bundle branch block (RBBB), the onset of intrinsic electrical activity takes place in the left ventricle. Since the electrical impulses originated in the opposite ventricular chamber and must travel through the Purkinje system and myocardium, the right ventricle is depolarized much later than the left. This delay is added to the electro-mechanical lag, prolonging PEP. Right ventricular PEP, in consequence, will be longer if the electrical depolarization of the heart starts in the left ventricle.

A similar situation will take place in case of left ventricular extrasystoles. Variation of PEP may also occur when PEP is measured from an intrinsic beat as compared to a paced beat. An intrinsic QRS is sensed by the pacemaker from 20 to 50 ms after its onset, depending on sensitivity settings, dV/dt, and peak QRS voltage, whereas a pacing artifact is recognized right at its onset by the pacemaker algorithm. In this situation, a sensed beat will have a shorter PEP than a paced beat.

To avoid the inconveniences caused by pacing/sensing offset, bundle branch blocks, and even pseudo-fusion beats (a non-capturing pacing spike delivered on a non-sensed QRS), it becomes necessary to develop a system exclusively using a mechanical interval as an indicator of metabolic need.

SUMMARY OF THE INVENTION

The foregoing objects and advantages of the invention are achieved by providing a novel rate-responsive pacemaker using an intracardiac, exclusively mechanical interval, namely, the isovolumic contraction time (IVCT) as a control signal responsive to metabolic demands. This control signal proportional to IVCT is injected into the timing circuit of a standard rate adaptive pacemaker to enhance the pacer's ability to respond in direct relation to the patient's changing metabolic needs as he performs his daily activities. A typical configuration of a rate adaptive pacemaker using IVCT for rate control is described in which either the right or left heart IVCT may be used. Accordingly, the pacing rate of the pacemaker is determined by the duration of IVCT. Since pacing interval and IVCT are linearly related, a simple conversion factor can be used to transform the duration of IVCT into the duration of the pacemaker escape interval. Although both right and left heart IVCT may be used for rate control, for the sake of simplicity, only the right heart parameters will be described herein. The device is capable of operating in most of the available modes (VVIR, DDDR, DDIR, AAIR), and has provisions for multiprogrammability, data storage, bidirectional telemetry, among other standard functions.

To measure IVCT, the device has two inputs: one, signaling the onset of mechanical activation of the ventricle, which is the start of IVCT, and another, signaling the onset of ejection, the end of IVCT. The time interval between these two events is the duration of IVCT, which is processed by the pacemaker to determine the escape interval (pacing rate), through a simple conversion algorithm, analogous to what is available in my prior art U.S. Pat. No. 4,719,921. Onset and end points of IVCT are detected by biological sensors in the form of pressure, volume or flow transducers. Several combinations of these transducers may be used to measure onset of mechanical activation (start of IVCT) and onset of ejection (end of IVCT).

DESCRIPTION OF THE DRAWINGS

The aforementioned objects and advantages of the invention will become subsequently apparent and reside in the details of construction and operation as more fully hereinafter described and claimed, reference being had to the accompanying drawings forming a part thereof, wherein like numerals refer to like parts throughout.

DESCRIPTION OF THE PREFERRED EMBODIMENT

Figure 1:
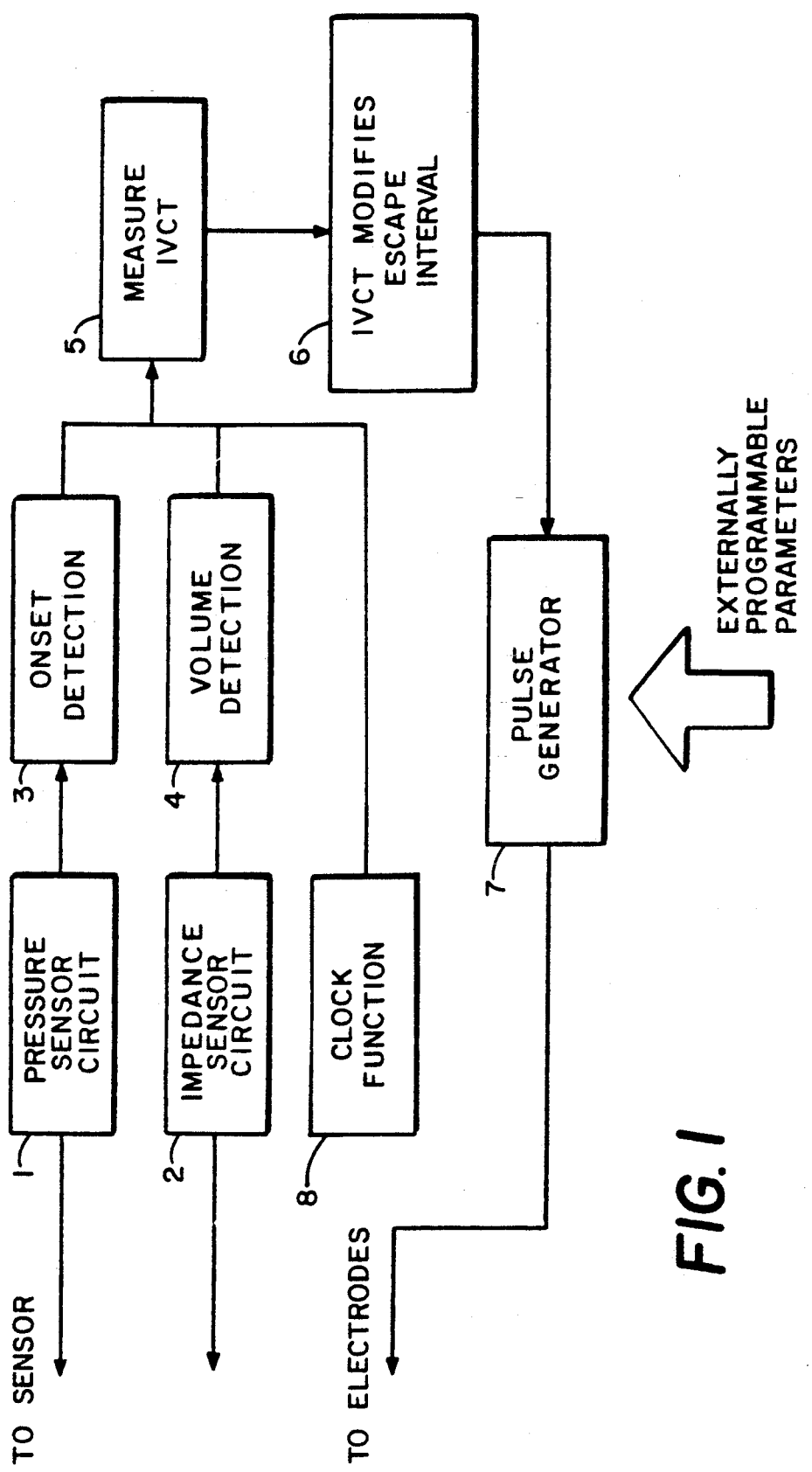
FIG. 1 depicts a functional block diagram of an apparatus in accordance with the teachings of the present invention, using one example of a combination of two sensors.

A preferred embodiment of the cardiac stimulating apparatus incorporating the present invention is illustrated by the block diagram of FIG. 1, in which onset and end points of IVCT are detected by biological sensors. These sensors may take the form of pressure, volume or flow transducers. Many readily available sensors could be used, as long as they provide an accurate signal and fulfill criteria for chronic implantability. Among these alternatives, onset of mechanical activation (start of IVCT) and onset of ejection (end of IVCT) may be detected by several combinations of these transducers. For clarity, a reduced list of possible sensor alternatives is provided:

1. ONSET OF MECHANICAL ACTIVATION (start of IVCT): Several biological signals and corresponding sensors may be utilized for the detection of the onset of contraction of the right ventricle, including:

(a) Onset of pressure rise (pressure transducer): A piezo-electric semiconductor embedded in the pacing lead, close to the tip, can be used as an indicator of the onset of IVCT, by signaling an abrupt pressure rise. It is known that during IVCT, as its name implies, ventricular volume does not change (isovolumetric) although there is ongoing contraction of the myocardium which increases the pressure.

(b) Onset of myocardial motion (impedance transducer): Driving a low-current AC signal through the heart via standard bipolar pacing electrodes permits the detection of impedance changes associated with volume changes. Ideally, the driving signal should be directed to the heart through a pair of electrodes different from those used for sensing. This configuration provides the best signal to noise ratio and gives an accurate representation of instantaneous volume. If driving the carrier and sensing are done from the same pair of electrodes, the system is more sensitive to local motion, producing distortion of the volume waveform. Local motion occurs when myocardial fibers contract in the vicinity of the electrode, producing significant overall impedance changes. Local motion indicates the very onset of ventricular activation, since the initial events taking place between the endocardium and electrode are a reflection of heart shape change but not of volume change.

(c) Tricuspid valve closure (sound transducer): Closure of the tricuspid valve produces a distinctive high frequency sound detectable with a piezo-electric microphone embedded in the pacing lead in the vicinity of the tricuspid valve. It could be used as an indication of the onset of mechanical activation. Although it follows the onset of contraction, the error is small, and for practical purposes it could be considered equivalent to the true onset of mechanical activation.

2. ONSET OF EJECTION (end of IVCT):

(a) Reduction of ventricular volume (impedance method): For the right ventricle, the most efficacious means of detecting the onset of ejection with an implantable device is by the impedance method. An abrupt impedance rise is indicative of an abrupt volume decrease, which in turn is a manifestation of the onset of ventricular emptying (ejection).

(b) Peak dP/dt (pressure transducer): The peak rate of pressure rise in the right ventricle is closely associated with the onset of ejection. During IVCT, ventricular pressure rises without volume changes, until the pulmonic valve opens. At this point, ejection begins and the rate of rise of pressure slows down. Generally, peak right ventricular dP/dt may either coincide with the onset of ejection, may precede it slightly or may closely follow it.

Given the above alternatives, the IVCT controlled pacemaker may utilize any of the following combinations to obtain the value of IVCT for rate control:

1. Pressure transducer, used for the onset of ventricular contraction and for the onset of ejection, as determined from its first derivative (dP/dt): IVCT is the time interval from the onset of pressure rise (contraction) to the peak dP/dt (onset of ejection). With this configuration a pressure transducer is used for detection of both endpoints.

2. Pressure transducer used for the onset of contraction, impedance transducer for the onset of ejection: With this configuration a lead comprising a set of conventional pacing electrodes and an embedded pressure transducer in the same lead is necessary.

3. Impedance transducer for the onset and end of IVCT: With this configuration a standard bipolar or unipolar pacing lead could be used.

4. Sound transducer (microphone) for the onset of contraction, impedance transducer for the onset of ejection: This system is similar to #2, with the exception that a sound transducer is used instead of the pressure transducer. In fact, the same piezo-electric semiconductor may be used for sound, pressure and dP/dt. Other combinations are also possible, but the four mentioned above are the most practical ones.

Referring now to FIG. 1, an example of a system using a dual transducer configuration (pressure and volume) is described. Other systems using a single transducer configuration, as shown above, may be utilized as well. The system described uses standard biological sensors, lead electrodes and externally programmable pacing parameters, as known in the art.

The pressure sensor signal is processed in block 1. The sensor may be of the piezoelectric type, as known in the prior art (U.S. Pat. No. 4,485,813), and embedded near the tip of the pacing lead. Simultaneously, block 2 delivers a constant current carrier signal to the lead electrodes and receives the resulting impedance signal, which is directed to block 4 for the detection of ventricular volume, in a manner similar to the teachings of U.S. Pat. No. 4,686,987. The onset of sudden volume reduction is detected and a corresponding signal is delivered to block 5. Block 3 detects the onset of pressure rise and also delivers a signal to block 5. IVCT is measured in block 5 a the time interval between the onset of pressure rise, as signaled by block 3 and the onset of ventricular ejection, as signaled by block 4. Logic circuitry present in block 6 adjusts the escape interval of the pacemaker pulse generator 7 in relation to the measured value of IVCT. Pulse generator 7 then delivers a pulsed discharge, via standard cardiac electrodes, in the known manner. A clock function 8 continuously registers clock pulses and increments a timing value.

Figure 2:
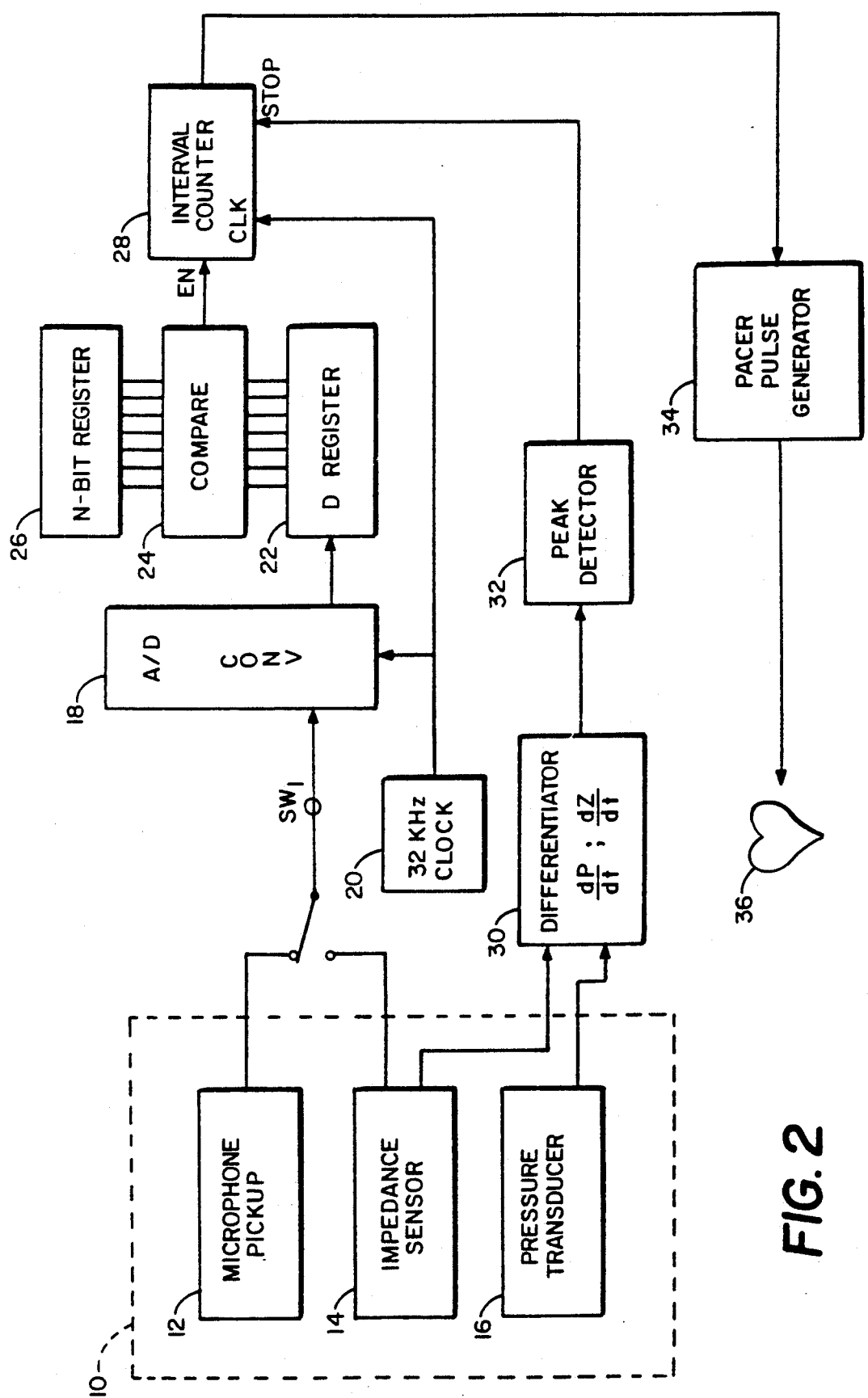
FIG. 2 is a functional block diagram of the logic means used in the present invention.

As described above, the onset or end of IVCT may be detected using impedance, pressure or sound methods. FIG. 2 depicts an implantable preferred means for performing the comparator and differentiator functions required to obtain the timing values that enable measurement of the duration of IVCT. In the example described, either closure of the tricuspid valve or the change in impedance which occurs with onset of contraction of the ventricle are selected to mark the onset of IVCT. In this example, measurement of pressure marks the end of IVCT.

Sensors, generally designated as 10, include microphone 12 for sensing the sound emitted as the tricuspid valve closes, impedance sensor 14 for sensing instantaneous impedance values within the ventricular cavity, and pressure transducer 16 for sensing instantaneous pressure values. Programmable switch $SW_1$ selects between sound 12 or impedance 14 detection means. Whether a microphone pickup is used to detect sound, or an impedance sensing circuit is used to detect instantaneous impedance within the ventricle, an analog signal train is delivered to an A/D converter 18, such as a Delta Modulator. A/D converter 18 digitizes the analog signal into a serial bit stream. A 32 kHz clock 20 is coupled with the A/D converter 18 and the data is clocked into a register 22 whose data output lines are fed into one set of inputs to a comparator 24. A predetermined reference or threshold value is programmed into N-bit register 26, whose outputs are also fed into comparator 24. When a match occurs between the preprogrammed reference or threshold value from register 26 and the data value from register 22, the comparator 24 outputs a "start" signal to interval counter 28. Using clock 20, the interval counter 28 initiates a count of regularly occurring clock pulses.

In this example, a pressure transducer sensing circuit 16 is used to define the onset of ventricular ejection, signaling the end of the IVCT period. As shown at 16, the pressure sensing circuit produces a p vs. t analog waveform. This signal is fed to differentiater 30, whereby it is differentiated using standard methods and the resultant signal is fed to peak detector 32. At peak detector 32, the maximal dP/dt signal is selected. This signal is used to define the onset of contraction of the ventricle, the end of IVCT. Thus, it is fed to interval counter 28, wherein this signal is used to inhibit the counter, ceasing the accumulation of regularly occurring clock pulses. The timing value held in interval counter 28 at this moment is thus captured. Since it is directly proportional to the duration of IVCT, this signal can be injected directly into a standard digital pacer pulse generator 34. Within the control means of digital pacer pulse generator 34, the IVCT duration signal developed in counter 28 is used to modify the pacer's escape interval for applying stimulating pulses to heart 36.

If analog RC timing circuitry is used in the pacer, the count in counter 28 can be converted in a D/A converter to an analog current proportional to IVCT and injected into the timing capacitor to vary the pacer's escape interval.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. In a cardiac pacemaker of the type including a pulse generating means for applying stimulating pulses to tissue, said pulse generating means including rate control means for controlling timing of delivery of said stimulating pulses, the improvement comprising:
    (a) means for detecting a first IVCT event using the timing of the onset of mechanical contraction of the ventricle of a heart as an indicator of the start of the physiological isovolumic contraction period;
    (b) means for detecting a second IVCT event using the timing of the onset of ejection of blood from the ventricle as an indicator of the end of the physiological isovolumic contraction period;
    (c) control signal generating means for developing a control signal proportional to the time difference between said first and second IVCT events as an indicator of duration of isovolumic contraction time; and
    (d) means for injecting said control signal into said rate control means for altering the timing of the delivery of said stimulating pulses as a function of IVCT.

2. The cardiac pacemaker as in claim 1, wherein the means for detecting said first and second IVCT events further comprises an impedance sensor for indicating the start of the physiological isovolumic contraction period and the timing of the onset of ejection of blood from the ventricle.

3. The cardiac pacemaker as in claim 1, wherein the means for detecting said first and second IVCT events further comprises a pressure sensor for indicating the start of the physiological isovolumic contraction period and an impedance sensor for determining the timing of the onset of ejection of blood from the ventricle.

4. The cardiac pacemaker as in claim 1, wherein the means for detecting said first and second IVCT events further comprises a sound sensor for indicating the start of the physiological isovolumic contraction period and an impedance sensor for determining the timing of the onset of ejection of blood from the ventricle.

5. The cardiac pacemaker as in claim 1, wherein the means for detecting said first and second IVCT events further comprises an impedance sensor for indicating the start of the physiological isovolumic contraction period and a pressure sensor for determining the timing of the onset of ejection of blood from the ventricle.

6. The cardiac pacemaker as in claim 1, wherein the means for detecting said first and second IVCT events further comprises a pressure sensor for indicating the start of the physiological isovolumic contraction period and means for determining maximal rate of change of pressure for indicating the end of the physiological isovolumic contraction period.

7. The cardiac pacemaker as in claim 1, wherein the means for detecting said first and second IVCT events further comprises a sound sensor for indicating the start of the physiological isovolumic contraction period and a pressure sensor having differentiating means for determining the timing of the onset of ejecting of blood from the ventricle.

8. In a cardiac pacemaker of the type including a pulse generating means for applying stimulating pulses to tissue, said pulse generating means including rate control means for controlling timing of said stimulating pulses, the improvement comprising:
    (a) impedance detecting means for sensing instantaneous impedance values and comparator means coupled to the impedance detecting means for comparing said instantaneous impedance values with a reference vale for determining a first timing value indicating the timing of the onset of change in instantaneous impedance value from said reference value as an indicator of the onset of contraction of the ventricle of the heart;
    (b) means coupled to the impedance detecting means for determining a second timing value indicating the onset of abrupt rise in impedance within the ventricular cavity of the heart as an indicator of the onset of ventricular ejection;
    (c) control signal generating means for developing a control signal related to the difference between said first and second timing values as an indicator of duration of isovolumic contraction time; and
    (d) means for injecting said control signal into said rate control means for altering the timing of the delivery of said stimulating pulses in proportion to said control signal and as a function of IVCT.

9. In a cardiac pacemaker of the type including a pulse generating means for applying stimulating pulses to tissue, said pulse generating means including rate control means for controlling timing of said stimulating pulses, the improvement comprising:
    (a) impedance detecting means for sensing instantaneous impedance values and comparator means coupled to the impedance detecting means for comparing said instantaneous impedance values with a reference value for determining a first timing value indicating the timing of the onset of change in impedance value from said reference value as an indicator of the onset of contraction of the ventricle of the heart;

(b) pressure sensing means coupled to said impedance detecting means for sensing instantaneous pressure values within the ventricular cavity of the heart and differentiator means coupled to said pressure sensing means for differentiating said instantaneous pressure values and for determining a second timing value indicating maximal rate of change of pressure as a measure of the onset of ventricular ejection;

(c) control signal generating means for developing a control signal related to the difference between said first timing value as an indicator of the timing of onset of contraction of the ventricle and said second timing value as an indicator of the timing of onset of ventricular ejection, said control signal being an indicator of duration of isovolumic contraction time; and (d) means for injecting said control signal into said rate control means for altering the timing of the delivery of said stimulating pulses in proportion to said control signal and as a function of IVCT.

10. In a cardiac pacemaker of the type including a pulse generating means for applying stimulating pulses to tissue, said pulse generating means including rate control means for controlling timing of said stimulating pulses, the improvement comprising:

(a) pressure sensing means for sensing instantaneous pressure values within the ventricular cavity of the heart and comparator means coupled to the pressure sensing means for comparing said instantaneous pressure values and for determining a first timing value indicating when the rate of rise of the instantaneous pressure values exceeds a predetermined threshold value as a measure of the onset of contraction of the ventricle of the heart, and differentiator means for differentiating said instantaneous pressure values and for determining a second timing value indicating maximal rate of change of pressure as a measure of the onset of ventricular ejection;

(b) control signal generating means for developing a control signal related to the difference between said first and second timing values as an indicator of duration of isovolumic contraction time; and (c) means for injecting said control signal into said rate control means for altering the timing of the delivery of said stimulating pulses in proportion to said control signal and as a function of IVCT.

11. In a cardiac pacemaker of the type including a pulse generating means for applying stimulating pulses to tissue, said pulse generating means including rate control means for controlling timing of said stimulating pulses, the improvement comprising:

(a) pressure sensing means for sensing instantaneous pressure values within a ventricular cavity of the heart and comparator means coupled to the pressure sensing means for comparing said instantaneous pressure values and for determining a first timing value indicating when the rate of rise of the instantaneous pressure values exceeds a predetermined threshold value as a measure of the onset of contraction of the ventricle of the heart;

(b) impedance means for determining a second timing value indicating the onset of abrupt rise in impedance within the ventricular cavity of the heart as an indicator of the onset of ventricular ejection;

(c) control signal generating means for developing a control signal related to the difference between said first timing value as an indicator of the timing of onset of contraction of the ventricle and said second timing value as an indicator of the timing of onset of ventricular ejection, said control signal being an indicator of duration of isovolumic contraction time; and (d) means for injecting said control signal into said rate control means for altering the timing of the delivery of said stimulating pulses in proportion to said control signal and as a function of IVCT.

12. In a cardiac pacemaker of the type including a pulse generating means for applying stimulating pulses to tissue, said pulse generating means including rate control means for controlling timing of said stimulating pulses, the improvement comprising:

(a) sound detection means for developing a first timing value by sensing the timing of tricuspid valve closure, which indicates the onset of contraction of a ventricle of the heart, and impedance means for determining a second timing value indicating the onset of abrupt rise in impedance value within the ventricular cavity of the heart as an indicator of the onset of ventricular ejection;

(b) control signal generating means for developing a control signal related to the difference between said first timing value as an indicator of the timing of onset of contraction of the ventricle and said second timing value as an indicator of the timing of onset of ventricular ejection, said control signal being an indicator of duration of isovolumic contraction time; and (c) means for injecting said control signal into said rate control means for altering the timing of the delivery of said stimulating pulses in proportion to said control signal and as a function of IVCT.

13. In a cardiac pacemaker of the type including a pulse generating means for applying stimulating pulses to tissue, said pulse generating means including rate control means for controlling timing of said stimulating pulses, the improvement comprising:

(a) sound detection means for developing a first timing value by sensing the timing of tricuspid valve closure, which indicates the onset of contraction of a ventricle of the heart, and pressure sensing means for sensing instantaneous pressure values within the ventricular cavity of the heart and differentiator means for differentiating said instantaneous pressure values and for determining a second timing value indicating maximal rate of change of pressure as a measure of the onset of ventricular ejection;

(b) control signal generating means for developing a control signal related to the difference between said first timing value as an indicator of the timing of onset of contraction of the ventricle and said second timing value as an indicator of the timing of onset of ventricular ejection, said control signal being an indicator of duration of isovolumic contraction time; and (c) means for injecting said control signal into said rate control means for altering the timing of the delivery of said stimulating pulses in proportion to said control signal and as a function of IVCT.

* * * * *